US011179408B2

(12) United States Patent
Saldanha et al.

(10) Patent No.: US 11,179,408 B2
(45) Date of Patent: Nov. 23, 2021

(54) USE OF CYANOGLUCOSIDES AND PHARMACEUTICAL FORMULATIONS THEREOF IN THE TREATMENT OF DIABETES

(71) Applicants: UNIVERSIDADE ESTADUAL PAULISTA JULIO DE MESQUITA FILHO, Sao Paulo (BR); UNIVERSITE DE GENEVE, Geneva (CH)

(72) Inventors: Luiz Leonardo Saldanha, Bauru (BR); Anne Ligia Dokkedal Bosqueiro, Bauru (BR); Jose Roberto Bosqueiro, Bauru (BR); Nathalia Aparecida De Paula Camaforte Henriques, Bauru (BR); Priscilla Maria Ponce Vareda, Bauru (BR); Wagner Vilegas, Sao Vicente (BR); Emerson Ferreira Queiroz, Geneva (CH); Laurence Marcourt, Geneva (CH); Jean-Luc Wolfender, Geneva (CH)

(73) Assignees: UNIVERSITÉ DE GENÈVE, Genèva (CH); UNIVERSIDADE ESTADUAL PAULISTA JÚLIO DE MESQUITA FILHO, Sao Paulo (BR)

(*) Notice: Subject to any disclaimer, the term of this patent is extended or adjusted under 35 U.S.C. 154(b) by 0 days.

(21) Appl. No.: 16/313,560

(22) PCT Filed: Jun. 28, 2016

(86) PCT No.: PCT/BR2016/050148
§ 371 (c)(1),
(2) Date: Dec. 27, 2018

(87) PCT Pub. No.: WO2018/000057
PCT Pub. Date: Jan. 4, 2018

(65) Prior Publication Data
US 2019/0160085 A1    May 30, 2019

(51) Int. Cl.
| A61K 31/7034 | (2006.01) |
| A61P 3/10 | (2006.01) |
| A61P 3/00 | (2006.01) |
| A61K 45/06 | (2006.01) |
| C07H 15/207 | (2006.01) |
| A61K 9/00 | (2006.01) |

(52) U.S. Cl.
CPC ........ *A61K 31/7034* (2013.01); *A61K 9/0053* (2013.01); *A61K 45/06* (2013.01); *A61P 3/00* (2018.01); *A61P 3/10* (2018.01); *C07H 15/207* (2013.01)

(58) Field of Classification Search
CPC ...... A61K 31/7034; A61K 9/0053; A61P 3/10
USPC .......................................................... 514/25
See application file for complete search history.

(56) References Cited

U.S. PATENT DOCUMENTS

2004/0170714 A1    9/2004    Buchholz et al.

FOREIGN PATENT DOCUMENTS

CN         101773553         7/2010

OTHER PUBLICATIONS

Das (Current Hypertension Reports 2004, 6:66-73).*
Camaforte, N. A. D. P. et al. "Hypoglycaemic activity of *Bauhinia holophylla* through GSK3-β inhibition and glycogenesis activation" *Pharmaceutical Biology*, 2019, p. 269-279, vol. 57, No. 01.
Athikomkulchai, S. et al. "Chemical Constituents of *Bauhinia sirindhorniae*" *Natural Medicines*, 2003, pp. 150-153, vol. 57, No. 4.
Challal, S. et al. "Rational and Efficient Preparative Isolation of Natural Products by MPLC-UV-ELSD based on HPLC to MPLC Gradient Transfer" *Planta Medica*, 2015, pp. 1-9, vol. 81, No. 17.
Lewis G. P. et al. "Tribe Cerideae" 2005, pp. 57-67, Royal Botanic Gardens, Kew.
Russo, E. M. K. et al. "Clinical Trial of *Myrcia uniflora* and *Bauhinia forficata* Leaf Extracts in Normal and Diabetic Patients" *Brazilian Journal of Medical and Biological Research*, 1990, pp. 11-20, vol. 23.
Wunderlin, R. et al., "Reorganization of the Cercideae (*Fabaceae: Caesalpinioideae*)" *Biologiske Skrifter*, 1987, pp. 1-21, vol. 28.
Oliveira, F. et al. "Alguns vegetais brasileiros empregados no tratamento da diabetes" *Rev. Bras. Farmacogn.*, 1989, pp. 170-196, vol. 2-3-4.
Plouvier, V. "Présence de Lithospermoside dans le *Cercis siliquastrum*" *Phytochemistry*, 1978, p. 1010, vol. 17.
Banks, H. et al. "Palynological contribution to the systematics and taxonomy of *Bauhinia* s.l. (Leguminosae: Cercideae)" *South African Journal of Botany*, 2013, pp. 219-226, vol. 89.
Bruneau, A. et al. "Phylogenetic Relationships in the Caesalpinioideae (Leguminosae) as Inferred from Chloroplast trnL Intron Sequences" *Systematic Botany*, 2001, pp. 487-514, vol. 26, No. 3.
Bruneau, A. et al. "Phylogenetic patterns and diversification in the caesalpinioid legumes" *Botany*, 2008, pp. 697-718, vol. 86.

(Continued)

*Primary Examiner* — Shaojia A Jiang
*Assistant Examiner* — Michael C Henry
(74) *Attorney, Agent, or Firm* — Saliwanchik, Lloyd & Eisenschenk (57) ABSTRACT

The present invention relates to the use of cyanoglucoside according to formula (I) and formulations thereof in the prevention and/or treatment of diabetes and/or metabolic syndrome; wherein $R_1$, $R_2$ and $R_3$ are independently selected from an optionally substituted mono- or di-saccharide, —O—$R_4$, —O—C(O)—$R_4$ and halogen, such as Cl, F or Br, wherein $R_4$ is selected from H, alkyl, such as methyl, as well as tautomers, geometrical isomers, optically active forms, pharmaceutically acceptable salts and pharmaceutically active derivative thereof.

14 Claims, 6 Drawing Sheets

(56) References Cited

OTHER PUBLICATIONS

Fort, D. M. et al. Lithospermoside from *Bauhinia fassoglensis* (Fabaceae) *Biochemical Systematics and Ecology*, 2001, pp. 439-441, vol. 29.

Hao, G. et al. "Phylogenetics of *Bauhinia* subgenus *Phanera* (Leguminosae: Caesalpinioideae) based on ITS sequences of nuclear ribosomal DNA" *Bot. Bull. Acad. Sin.*, 2003, pp. 223-228, vol. 44.

Josien-Lefebvre, D. et al. "Total Synthesis of (—)-Lithospermoside" *Helvetica Chimica Acta*, 2003, pp. 661-672, vol. 86.

Josien-Lefebvre, D. et al. "Total Synthesis of (2Z)-[(4R,5R,6S)-6-(β-D-Glucopyranosyloxy)-4,5-dihydroxycyclohex-2-en-1-ylidene]ethanenitrile, a Cyanoglucoside from *Ilex warburgii*" *Helvetica Chimica Acta*, 2007, pp. 19-30, vol. 90.

Moreira, F. F. et al. "The systematic value of pollen morphology in trees and shrubs species of *Bauhinia* L. (*Caesalpinioideae*—subg. *Bauhinia*—sect. *Pauletia*) occurring in Brazil" *Acta Botanica Brasilica*, 2013, pp. 400-417, vol. 27, No. 2.

Niranjan Kumar, A. et al. "Rare cyano glucosides from *Coldenia procumbens* Linn." *Journal of Chemical and Pharmaceutical Research*, 2013, pp. 1394-1397, vol. 5, No. 12.

Pepato, M. T. et al. "Anti-diabetic activity of *Bauhinia forficata* decoction in streptozotocin-diabetic rats" *Journal of Ethnopharmacology*, 2002, pp. 191-197, vol. 81.

Rozza, A. L. et al. "Antiulcerogenic Activity and Toxicity of *Bauthinia holophylla* Hydroalcoholic Extract" *Evidence-Based Complementary and Alternative Medicine*, 2015, pp. 1-9, vol. 2015, Article ID 439506.

Silva, T. M. S. et al. "Riachin, a New Cyanoglucoside from *Bauhinia pentandra* and its Antioxidant Activity" *Chemistry of Natural Compounds*, Sep. 2013, pp. 685-690, vol. 49, No. 4.

Sinou, C. et al. "The genus *Bauhinia* s.l. (Leguminosae): a phylogeny based on the plastid trnL-trnF region" *Botany*, 2009, pp. 947-960, vol. 87.

Sosa, A. et al. "Structure of a Cyanoglucoside of *Lithospermum Purpureo-Caeruleum*" *Phytochemistry*, 1977, pp. 707-709, vol. 16.

De Sousa, E. et al. "Hypoglycemic Effect and Antioxidant Potential of Kaempferol-3,7-O-(α)-dirhamnoside from *Bauhinia forficata* Leaves" *J. Nat. Prod.* 2004, pp. 829-832, vol. 67, No. 5.

Wunderlin, R. P. "New Combinations in *Schnella*(Fabaceae: Caesalpiniodeae: Cercideae)" *Phytoneuron*, 2010, pp. 1-5, vol. 49.

Yamasaki, K. "Non-Cyanogenic Cyanoglucosides" *Studies in Plant Science*, 1998, pp. 335-345, vol. 6.

Zhang, D. A cladistic analysis of *Bauhinia* L. (Leguminosae: Cercideae), *Chinese Journal of Botany*, Jan. 1995, pp. 55-64, vol. 7, No. 1 (Abstract only).

Zhang, H. et al. "Cyano- and Nitro-containing Compounds from the Roots of *Semiaquilegia adoxoides*" *Chinese Journal of Chemistry*, 2004, pp. 1200-1203, vol. 22, No. 10.

Written Opinion in International Application No. PCT/BR2016/050148, dated Sep. 6, 2016, pp. 1-6.

Patel, N. et al. "Evaluation of Antidiabetic Activity of *Coldenia procumbens* in Alloxan-Induced Diabetes in Rat" *Journal of Herbal Pharmacotherapy*, 2007, pp. 13-23, vol. 7, No. 1.

Silva, K. L. et al. "Plantas Do Gênero *Bauhinia*: Composição Química e Potencial Farmacológico" *Quim. Nova*, 2002, pp. 449-454, vol. 25, No. 3.

European Search Report dated Feb. 14, 2020 for European Patent Application No. 16906503.4, pp. 1-10.

\* cited by examiner

Figure 4

USE OF CYANOGLUCOSIDES AND PHARMACEUTICAL FORMULATIONS THEREOF IN THE TREATMENT OF DIABETES

CROSS-REFERENCE TO RELATED APPLICATION

This application is the U.S. national stage application of International Patent Application No. PCT/BR2016/050148, filed Jun. 28, 2016.

FIELD OF INVENTION

The present invention applies to the use of compounds from the class of cyanoglucosides for the treatment of diabetes.

BACKGROUND OF THE INVENTION

The body's cells constantly need energy to perform numerous metabolic reactions inherent to the activity of each cell type.

The metabolic cycle begins with the intake and absorption of dietary nutrients. Glucose from the feed, among other destinations, may be stored in various forms in body tissues like liver, adipose tissue and muscle. Such processes are mediated by the action of insulin in response to increased glucose in the bloodstream.

Insulin exerts important cellular, metabolic and mitogenic effects mediated by its receptor, which is present in nearly all tissues of vertebrates. Disturbances in glucose metabolism and insulin production can lead to complications such as diabetes.

Diabetes mellitus (DM) is a heterogeneous group of metabolic disorders characterized by chronic hyperglycemia resulting from defects in the insulin secretion and/or action, which may lead to alterations in the metabolism of carbohydrates, lipids and proteins.

The classification proposed by the World Health Organization (WHO) and the American Diabetes Association (ADA) includes four clinical DM classes: DM type 1 (DM1), DM type 2 (DM2), other specific types of DM and Gestational DM.

DM1 is due to absolute deficiency in insulin production, generally caused by autoimmune process that leads to destruction of the beta cells of pancreatic islets. Patients with this type of diabetes rely on treatment with exogenous insulin to sustain life. Most of these individuals develop anti-pancreatic islet antibodies (ICA), anti-insulin antibodies (IAA), antibody to the 65 kDa isoform of glutamic acid decarboxylase (GAD65) and antigens associated 1A-2A insulinoma. The highest incidence of type 1 diabetes occurs in childhood and adolescence.

The type 2 diabetes is due to pancreatic relative deficiency in insulin production associated with reduced tissue sensitivity to the hormone, also known as insulin resistance. Insulin resistance occurs when a normal concentration of insulin produces an inappropriate and/or poor biological response in peripheral tissues such as adipose and muscle tissue. This insulin resistance occurs by several factors such as defects in insulin action due to the lower number of receptors or lower affinity of these by insulin and by the reduction in the amount of glucose transporter proteins (GLUTs) or translocation of these from the cytoplasm to the membrane, the latter being considered the most important. The transition from insulin resistance to DM is determined primarily by the inability of the pancreas to adequately increase insulin secretion in response to hyperglycemia.

The main symptoms of diabetes include increased urination (polyuria), increased fluid intake (polydipsia), increased food intake (polyphagia) and significant weight loss. If untreated, it can lead to many complications including retinopathy with possible damage to vision, nephropathy that may lead to renal failure, and peripheral neuropathy with increased risk for foot ulcers and amputations. Patients with diabetes are more likely to develop diseases like atherosclerosis and peripheral arterial disease due to disturbances in lipid metabolism.

Current treatments for DM include insulin, through the use of exogenous insulin, and administration of allopathic drugs such as sulfonylureas (e.g. glyburide), biguanides (e.g. metformin) and alpha-glucosidase inhibitors (e.g. acarbose and miglitol), which may or may not be administered together.

The oral hypoglycemic agents exert their effects in lowering blood glucose levels through a variety of mechanisms including reduction of hepatic glucose production (metformin), increased secretion of insulin by pancreatic beta cells (insulin secretagogues such as the sulfonylureas), improvement of insulin sensitivity (thiazolidinedione and metformin) and inhibition of intestinal digestion and absorption of glucose (alpha-glucosidase inhibitors such as acarbose and miglitol).

The class of sulphonylureas such as chlorpropamide, glibenclamide, gliclazide, glipizide, and glimeperide, are hypoglycaemic drugs that act directly in the pancreas, increasing insulin secretion. These drugs do not affect the sensitivity to insulin in peripheral tissues. Its use, however, can cause undesirable effects such as hypoglycemia, weight gain, and in the long term kidney and liver damage.

Thiazolodinediones such as rosiglitazone and pioglitazone, are sensitizing agents of insulin action, since they increase the expression of genes encoding proteins involved in glucose and lipid metabolism. Studies in animal models have shown that thiazolodinediones preserve and improve the function of pancreatic beta cells. On the other hand, its use causes adverse effects such as weight gain, edema, hepatotoxicity, and congestive heart failure.

The leaves of *Bauhinia* species, particularly *Bauhinia forticata* are traditionally used as a tea for the treatment of diabetes in Brazil and in Chile. However, *Bauhinia forticata* is rather difficult to identify with certainty since the taxonomic organization of *Bauhinia* s.l. is especially complex considering the number of different organization proposals along decades. Many studies based on morphological (Wunderlin et al., 1987, Biologiske Skrifter 28, 1-40 and Zhang, 1995, Chinese Journal of Botany 7, 52-64) and molecular (Bruneau et al., 2001, Systematic Botany 26, 487-514; Bruneau et al., 2008, Botany 86, 697-71 and Hao et al., 2003, Botanical Bulletin of Academia Sinica 44, 223-228) data results in different taxonomic relations. Researchers have recognized *Bauhinia* s.l. either as a single large genus comprising 300 to 350 species (e.g. Wunderlin et al., 1987, supra), or as several distinct genera (Lewis and Forest, 2005, Royal Botanic Gardens, Kew, pp. 57-67 and Sinou et al., 2009, Botany 87, 947-960). *Bauhinia* s.l was recently subdivided into 9 genera based on phylogenetic data:*Bauhinia* s.str., Barklya, Brenierea, Gigasiphon, Lysiphyllum, Phanera, Piliostigma, Schnella (American Phanera) and Tylosema. (Hao et al., 2003, supra; Sinou et al., 2009, supra and Wunderlin, 2010, Phytoneuron 49, 1-5). Besides phylogenetic studies, the clear infrageneric taxonomic organization of some *Bauhinia* species is only possible nowadays based on pollen attributes obtained by electron microscopy scanning (Banks et al., 2013, South African Journal of Botany 89, 219-226; Moreira et al., 2013, Acta Bot. Bras. 27-2). Thus, the examination of vegetative and reproductive characters concerning the identification of *Bauhinia* at specie level is complex and needs to be confirmed by specialists in *Bauhinia* taxonomy.

Extracts from this plant has been the object of a large number of publications. Some of the scientific works describe the in vivo hypoglycemic activity of the plant extract for the treatment of diabetes.

US 2004/0170714 describes the use of *Bauhinia forticata* extract for treating diabetes type 2 where the activity was attributed to the presence of at least a flavone or a flavonoid.

Pepato et al., 2002, *Journal of Ethopharmacology*, 81, 191-197, describe the antidiabetic effect of *Bauhinia forticata* decoction for treating diabetes in rats.

Russo et al., 1990, Brazilian Journal of Medical and Biological Research, 23, 11-20, describe a clinical study with extracts of *Myrcia uniflora* and *Bauhinia forticata* in the treatment of diabetic patients.

In all the documents cited above, *Bauhinia forticata* extracts are mentioned. However, despite that the hypoglycemic activity of *Bauhinia* species have been outstanding for a long time, few studies have been carried out with respect to the chemical content of this species. In 2004, Souza et al., Journal of Natural Products, 67, 829-832, describe the in vivo and in vitro effects of kaempferol-3,7-O—(R)-dirhamnoside (kaempferitrin), a major flavonoid compound of the n-butanol fraction from *Bauhinia forficata* leaves, on serum glucose levels, as well as its antioxidant potential. Oral administration of kaempferitrin led to a significant hypoglycemic effect in normal and in alloxan-induced diabetic rats. In normal rats, blood glucose lowering was observed only with the higher dose of kaempferitrin (200 mg/kg) 1 h after treatment. However, the hypoglycemic effect of kaempferitrin in diabetic rats was evident at all doses tested (50, 100, and 200 mg/kg), and this profile was maintained throughout the experimental period for both higher doses. Until now this is the only study that relates the biological activity of extracts from *Bauhinia forticata* to a particular compound.

Cyanogenic glycosides or cyanoglycosides account for approximately 90% of the wider group of plant toxins known as cyanogens. The main characteristic of these toxins is cyanogenesis, i.e. the formation of free hydrogen cyanide, and is associated with cyanohydrins that have been stabilized by glycosylation to form the cyanogenic glycoside. Examples of cyanogenic glycosides include linamarin from cassava and amygdalin from the seeds of stone fruit. Amygdalin and its semi-synthetic form laterile possess anticancer activities against colon, breast, cervical and prostate cancers. Lithospermoside ((2Z)-2-[(4R,5S,6S)-4,5-dihydroxy-6-[[(2S,3S,4R,5R,6S)-3,4,5-trihydroxy-6-(hydroxymethyl)-2-oxanyl]oxy]-1-cyclohex-2-enylidene] acetonitrile) belongs to the family of cyanogenic glycosides and is known for its antioxidant and anti-tumor properties and can be extracted from *Lithospermum officinale* or from *Cercis siliquastrum* (Plouvier et al., 1978, *Phytochemistry*, 17, 1010) or from *Lithospermum purpureo-caruleum* (Sosa et al., 1977, 6, 707-709).

Despite progress in therapy and patient management through lifestyle, diet and drug treatment, a great need still exists for compositions and methods for the successful treatment and management of diabetes.

SUMMARY OF THE INVENTION

The present invention is based on the unexpected finding that Lithospermoside can be extracted from *Bauhinia holophylla* and has a strong in vivo hypoglycemic activity about 30 times higher than metformin. This is the first time that the hypoglycemic activity was correlated to cyanoglucosides in general and in particular to Lithospermoside.

According to one aspect, the invention provides cyanoglucosides of the invention for use in the prevention and/or treatment of diabetes.

According to another aspect, the invention provides a use of cyanoglucosides for the preparation of a pharmaceutical formulation for use in the prevention and/or treatment of diabetes.

According to another aspect, the invention provides a pharmaceutical formulation comprising at least one cyanoglucoside of the invention combined with at least one co-agent useful in the prevention and/or treatment of diabetes, and at least one pharmaceutically acceptable carrier.

According to another aspect, is provided a method of treating or ameliorating diabetes, said method comprising administering in a subject in need thereof a therapeutically effective amount of cyanoglucoside of the invention or a mixture thereof or a pharmaceutical formulation thereof.

BRIEF DESCRIPTION OF THE FIGURES

FIG. 3: Effect of the treatment with Lithospermoside at a dose of 10 mg/kg on fasting blood glucose (G). CTLSAL: normoglycemic mice treated with saline (0.9% NaCl), STZSAL: diabetic mice treated with saline (0.9% NaCl), STZMET: diabetic mice treated with metformin at a dose of 300 mg/kg, LITHOS: diabetic mice treated with BH-21 diluted in saline at 10 mg/kg body weight. The animals were treated daily for 28 days. Data expressed as mean±standard error of the mean. ANOVA followed by Tukey post-test. a vs. CTLSAL, b vs. STZSAL, c vs. STZMET, N=8-12, $p<0.05$.

DETAILED DESCRIPTION OF THE INVENTION

The term "mono- or di-saccharide" as use herein refers to the presence of one or more sugars in positions $R_1$, $R_2$ or $R_3$ and include glucose, galactose, glucoronic acid, rhaminose, fructose, maltose, sucrose or any other modified sugar.

The term "alkyl" when used alone or in combination with other terms comprises a straight chain or branched C1-C8 alkyl which refers to monovalent alkyl groups having 1 to 8 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, n-heptyl, 2-methylhexyl, 3-methylhexyl, 4-methylhexyl, 5-methylhexyl, n-heptyl, n-octyl, n-nonyl, n-decyl, tetrahydrogeranyl, n-dodecyl, n-tridecyl, n-tetradecyl, n-pentadecyl, n-hexadecyl, n-octadecyl and the like. Preferably, these include C1-C6 alkyl, especially preferably C1-C4 alkyl, which, by analogy, refers respectively to monovalent alkyl groups having 1 to 6 carbon atoms and monovalent alkyl groups having 1 to 4 carbon atoms.

Unless otherwise constrained by the definition of the individual substituent, the term "substituted" refers to groups substituted with from 1 to 5 substituents selected from the group consisting of "$C_1$-$C_6$ alkyl," "amino," "halogen," hydroxy, mono- or di-saccharide, and the like. As used herewith the term "diabetes" refers to the chronic disease characterized by relative or absolute deficiency of insulin that results in glucose intolerance. This term covers diabetes mellitus, a group of metabolic diseases in which a person has high blood sugar level. As used herewith the term "diabetes" includes "diabetes mellitus type 1", a form of diabetes mellitus that results from autoimmune destruction of insulin-producing β cells of the pancreas, "diabetes mellitus type 2", a metabolic disorder that is characterized by high blood glucose in the context of insulin resistance and relative insulin deficiency, "gestational diabetes", a condition in which women without previously diagnosed diabetes exhibit high blood glucose levels during pregnancy, "neonatal diabetes", a rare form of diabetes that is diagnosed under the age of six months caused by a change in a gene which affects insulin production and "maturity onset diabetes of the young" (MODY), a rare form of hereditary diabetes caused by a mutation in a single gene.

The term "metabolic syndrome" refers to a cluster of syndromes including central obesity as reviewed in Kaur et al., 2014, *Cardiology Research and Practice*, ID943162 (e.g. BMI≥25 mg/m$^2$) plus at least two other conditions selected from dyslipidaemia (e.g. triglycerides ≥150 mg/DL and HDL≤40-50 mg/DL), elevated blood pressure (e.g. BP≥130/85 mm Hg), or insulin resistance. Metabolic syndrome directly increases the risk of cardiovascular disease type 2 diabetes and all cause mortality.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease.

The term "treatment" as used herein covers any treatment of a disease in a mammal, particularly a human, and includes: (a) preventing the disease from occurring in a subject who may be predisposed to the disease but has not yet been diagnosed as having it such as a preventive early asymptomatic intervention; (b) inhibiting the disease, i.e., arresting its development; or relieving the disease, i.e., causing regression of the disease and/or its symptoms or conditions such as improvement or remediation of damage. In particular, the methods, uses, formulations and compositions according to the invention are useful in the treatment of diabetes and/or in the prevention of evolution of diabetes. When applied to metabolic syndrome, prevention of a disease or disorder includes the prevention of the appearance or development of at least type-2 diabetes among the cluster of syndromes in an individual identified as at risk of developing metabolic syndrome.

When applied to diabetes, prevention of a disease or disorder includes the prevention of the appearance or development of diabetes in an individual identified as at risk of developing diabetes, for instance due to past occurrence of diabetes in the circle of the individual's relatives or to the observation of risk factors including age, genetic factors, obesity, lifestyle, etc. Also covered by the terms "prevention/treatment" of diabetes is the stabilization of an already diagnosed diabetes in an individual. By "stabilization", it is meant the prevention or delay of evolution of diabetes leading to complications such as diabetic ketoacidosis, hyperosmolar non-ketotic state, hypoglycemia, diabetic coma, respiratory infections, periodontal disease, diabetic cardiomyopathy, diabetic nephropathy, diabetic neuropathy, diabetic foot, diabetic retinopathy, coronary artery disease, diabetic myonecrosis, peripheral vascular disease, stroke, diabetic encephalopathy.

The term "subject" as used herein refers to mammals. For examples, mammals contemplated by the present invention include human, primates, domesticated animals such as cattle, sheep, pigs, horses, laboratory rodents and the like. The term "subject" covers juvenile individuals as well as adults. In particular, the subjects can be juvenile or adult subjects suffering from, or at risk of developing, any form of diabetes.

The term "effective amount" as used herein refers to an amount of a compound of the invention, composition or pharmaceutical formulation thereof according to the invention, that elicits the biological or medicinal response in a cell, tissue, system, animal or human that is being sought. In one embodiment, the effective amount is a "therapeutically effective amount" for the alleviation of the symptoms of the disease or condition being treated. In another embodiment, the effective amount is a "prophylactically effective amount" for prophylaxis of the symptoms of the disease or condition being prevented. The term also includes herein the amount of a compound of the invention sufficient to delay the onset, or reduce the progression of the disease, notably to delay, reduce or inhibit the complications of diabetes thereby eliciting the response being sought.

The term "efficacy" of a treatment according to the invention can be measured based on changes in the course of disease in response to a use or a method according to the invention. For example, the efficacy of a treatment of diabetes can be measured by a stable controlled glucose blood level, and/or periodic monitoring of glycated hemoglobin blood level.

The term "pharmaceutical formulation" refers to preparations which are in such a form as to permit biological activity of the active ingredient(s) to be unequivocally effective and which contain no additional component which would be toxic to subjects to which the said formulation would be administered.

Compounds of the Invention

Compounds of the invention are cyanoglucosides represented by the following formula (I):

(I)

wherein $R_1$, $R_2$ and $R_3$ are independently selected from an optionally substituted mono- or di-saccharide, —O—C(O)—$R_4$ and halogen such as Cl, F or Br, wherein $R_4$ is selected from H, alkyl such as methyl, as well as tautomers, geometrical isomers, optically active forms, pharmaceutically acceptable salts and pharmaceutically active derivative thereof.

According to a particular embodiment, $R_1$ is an optionally substituted monosaccharide.

According to another particular embodiment, $R_1$ is the following group:

(I')

Wherein $R_5$, $R_6$, $R_7$, and $R_8$ are independently selected from H, hydroxyl, amino, —C(O)—$R_9$ and —O—C(O)—$R_9$, wherein $R_9$ is alkyl such as methyl.

According to another particular embodiment, $R_1$ is of Formula (I'), wherein $R_5$ is hydroxyl and $R_6$, $R_7$, and $R_8$ are as described herein.

According to another particular embodiment, $R_1$ is of Formula (I'), wherein $R_6$ is hydroxyl and $R_5$, $R_7$, and $R_8$ are as described herein.

According to another particular embodiment, $R_1$ is of Formula (I'), wherein $R_7$ is hydroxyl and $R_5$, $R_6$, and $R_8$ are as described herein.

According to another particular embodiment, $R_1$ is of Formula (I'), wherein $R_8$ is hydroxyl and $R_5$, $R_6$, and $R_7$ are as described herein.

According to a further particular embodiment, $R_1$ is the following group:

According to another particular embodiment, $R_1$ is —O—$R_4$.

According to another particular embodiment, $R_2$ and $R_3$ are —O—$R_4$.

According to another particular embodiment, $R_4$ is H.

According to another particular embodiment, $R_2$ is OH.

According to another particular embodiment, $R_3$ is OH.

According to another particular embodiment, $R_2$ and $R_3$ are —OH.

According to a particular embodiment, is provided a cyanoglucoside of the invention which is lithospermoside:

(1)

as well as tautomers, geometrical isomers, enantiomers and racemic mixtures thereof pharmaceutically acceptable salts and pharmaceutically active derivative thereof.

According to another particular embodiment, $R_1$, $R_2$ and $R_3$ are OH.

According to another further particular embodiment, is provided a cyanoglucoside of the invention having the following structure:

(2)

as well as tautomers, geometrical isomers, enantiomers and racemic mixtures thereof pharmaceutically acceptable salts and pharmaceutically active derivative thereof.

According to another further particular embodiment, is provided a cyanoglucoside of the invention having the following structure:

(3)

as well as tautomers, geometrical isomers, enantiomers and racemic mixtures thereof pharmaceutically acceptable salts and pharmaceutically active derivative thereof.

Compositions

The invention provides pharmaceutical or therapeutic agents as compositions and methods for treating a patient, preferably a mammalian patient, and most preferably a human patient who is suffering from a medical disorder, and in particular diabetes.

In a particular embodiment, the invention provides a pharmaceutical formulation according to the invention for use as a medicament.

Pharmaceutical compositions of the invention can contain at least one compound according to the invention in any form described herein.

According to a particular aspect of the invention, pharmaceutical compositions of this invention contain at least 2% of an isolated cyanoglucoside of the invention.

According to another particular aspect of the invention, is provided a pharmaceutical composition comprising at least one cyanoglucoside as described herein, in a range of concentration ranging from 0.001 to 50%, in free form or in salt form (such as chlorates, sulfates or borates), associated with pharmaceutically acceptable excipients.

Compositions of this invention may further comprise one or more pharmaceutically acceptable additional ingredient(s) such as alum, stabilizers, antimicrobial agents, buffers, coloring agents, flavoring agents, adjuvants, and the like. The compositions according to the invention, together with a conventionally employed adjuvant, carrier, diluent or excipient may be placed into the form of pharmaceutical compositions and may be employed as solids, such as tablets or filled capsules, or liquids such as solutions, suspensions, ointments, emulsions, elixirs, or capsules filled with the same, films or gels, all for oral use, or in the form of sterile injectable solutions for parenteral (including subcutaneous) use by injection or continuous infusion. If desired, sustained-release compositions, e.g. sustained-release gels, films, and transdermal patches can be readily prepared. The compositions may also be formulated as a dry product for reconstitution with water or other suitable vehicle before use.

Compositions of this invention as liquid formulations including, but not limited to, aqueous or oily suspensions, solutions, emulsions, syrups, and elixirs may be for use as drops, for use in an injection, as a spray or impregnated in a nasal tampon.

Injectable compositions are typically based upon injectable sterile saline or phosphate-buffered saline or other injectable carriers known in the art. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. According to a particular embodiment, compositions according to the invention are injectable or inhalable.

Such liquid preparations may contain additives including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethyl cellulose, carboxymethyl cellulose, aluminum stearate gel, and hydrogenated edible fats. Emulsifying agents include, but are not limited to, lecithin, sorbitan monooleate, and acacia. Preservatives include, but are not limited to, methyl or propyl p-hydroxybenzoate and sorbic acid. Dispersing or wetting agents include but are not limited to poly(ethylene glycol), glycerol, bovine serum albumin, Tween®, Span®.

Further materials as well as formulation processing techniques and the like are set out in Part 5 of Remington's "The Science and Practice of Pharmacy", 22nd Edition, 2012, University of the Sciences in Philadelphia, Lippincott Williams & Wilkins, which is incorporated herein by reference.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Compositions of this invention may also be formulated for nasal delivery which may be in a form including, but not limited to powdered or liquid nasal spray, suspension, nose drops, a gel, film or ointment, through a tube or catheter, by syringe, by packtail, by pledget (small flat absorbent pad), by nasal tampon or by submucosal infusion.

The compounds of this invention can also be administered in sustained release forms or from sustained release drug delivery systems. A description of representative sustained release materials can also be found in the incorporated materials in Remington's Pharmaceutical Sciences.

Mode of Administration

Compositions of this invention may be administered in any manner including intravenous injection, oral route, mucosal administration (delivery to the mucosal surfaces of the nose, nasal passageways, nasal cavity; to the mucosal surfaces of the oral cavity including the gingiva, the floor of the oral cavity, the cheeks, the lips, the tongue, the teeth; intranasal administration (e.g. by spray, drops, powder, gel, film, inhalant or other means), dermal or transdermal administration (e.g. delivery to the skin including the face, neck, scalp, body or combinations thereof) for example by intradermal or subcutaneous injection, or combinations thereof.

In a particular embodiment, formulations of the compound of the invention according to the invention are oral formulations.

Combination

According to the invention, compounds of the invention and pharmaceutical formulations thereof can be administered alone or in combination with a co-agent useful in the prevention and/or treatment of diabetes, such as substances useful for treating, stabilizing, preventing, and/or delaying diabetes and/or insulin resistance e.g. for example a co-agent selected from Biguanides (e.g. Metformin), sodium-glucose co-transporter 2 (SGLT2) inhibitors (e.g. Canagliflozin or dapagliflozin, sulfonylurea drugs (e.g. glyburide).

The invention encompasses the administration of a compound of the invention and pharmaceutical formulations thereof to an individual prior to, simultaneously or sequentially with other therapeutic regimens or co-agents useful in the prevention and/or treatment of diabetes and/or insulin resistance (e.g. multiple drug regimens), in a therapeutically effective amount. A compound of the invention or the pharmaceutical formulations thereof that is administered simultaneously with said co-agents can be administered in the same or different composition(s) and by the same or different route(s) of administration.

According to one embodiment, is provided a pharmaceutical formulation comprising a compound of the invention combined with at least one co-agent useful in the prevention and/or treatment of diabetes, and at least one pharmaceutically acceptable carrier.

According to another embodiment, is provided a pharmaceutical formulation according to the invention wherein the derivative is lithospermoside.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Method for the Obtention of Compounds of the Invention

Compounds of the present invention can be obtained in essentially pure form from extracts of followed plant species: *Ochna schweinfurthiana, Coldenia procumbens, Semiaquilegia adoxoides, Lophira alata, Thalictrum orientale, Bauhinia fassoglensis, Cowania mexicana, Cercis siliquastrum, Lithospermum officinale, Lithospermum caeruleu, Griffonia simplicifolia, Ilex warburgii, Bauhinia holophylla* and *Bauhinia forticata* through standard methods of extraction.

To obtain the extract, biomass comprising leaves, stems, roots or fruits are extracted by percolation or soxhlet maceration by gases in the supercritical state as well as a mixture of these techniques.

The biomass (plant material) may be fresh and/or dried, powdered, ground, chopped and/or crumbly.

Optionally, the biomass is frozen before being processed. The prior freezing of plant material prevents thermal degradation caused by heat while passing through the electric mill.

The extraction is carried out by using 100% ethanol or 100% methanol or mixtures of ethanol:water or methanol:water in the ratio of 70:30, respectively.

The extract can be dried by spray drying technology (spray drying), at reduced pressure or at room temperature.

For spray drying, the inlet and outlet temperatures typically range between 150 and 190° C. and 90° C. and 80° C. respectively. In the drying at reduced pressure, it varies between 25 and 100° C.

The different compounds are separated and purified by chromatographic techniques with or without pressure, such as open column chromatography or low pressure chromatography, medium pressure chromatography or high pressure chromatography.

Liquid chromatography methods using reverse stationary phase (C-18) affords a good separation performance.

The extract can be fractionated by liquid chromatography pressure reverse phase with a solvent system having isocratic flow by successive plateaus 100% using water, methanol-water at a ratio of 5:95 to MeOH 100%. The cyanoglusosides may be eluted in more polar fractions.

The extract is fractionated by medium pressure chromatography (MPLC) reverse phase with a solvent system having isocratic flow of methanol-water at a ratio of 5:95, followed by gradual increase up to 100%.

From these fractions obtained, compounds of the invention are identified and isolated as single compound by spectroscopic methods (such as ultraviolet, 1D and 2D nuclear magnetic resonance, mass spectrometry at low and high resolution, as exemplified below.

Alternatively, compounds of the invention might be obtained by synthetic methods known for the synthesis of cyanoglucosides (Josien-Lefebvre et al., 2007, *Helvetica Chemica Acta*, 90, 19-28).

Patients

In an embodiment, patients according to the invention are patients suffering from or at risk of suffering from diabetes.

In a further embodiment, patients according to the invention are patients suffering from diabetes 2.

In another further embodiment, patients are suffering from metabolic syndrome.

Compounds according to the present invention comprise a compound according to Formula (I), its tautomers, its geometrical isomers, its optically active forms as enantiomers, diastereomers and its racemate forms, as well as pharmaceutically acceptable salts thereof.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. The invention having been described, the following examples are presented by way of illustration, and not limitation.

EXAMPLES

Example 1. Hydroalcoholic Extraction from *Bauhinia holophylla*

The fresh leaves from *Bauhinia holophylla* (COMPONENT SAMPLE ACCESS AUTHORIZATION AND SHIPMENT OF Brazilian GENETIC HERITAGE no 010468/2014-5) are introduced in to the oven with drying temperature controlled at 45° C. for 72 h. The dried material is pulverized and then triturated in electric knife mill.

The dried material at a concentration of 680 g is pre-swollen in 2 L of 70% EtOH (v/v) into a suitable container for 2 hours. After this period, the swollen plant material and 70% ethanol (v/v) in a 1:5 are added to the percolator. The flow of the percolator is adjusted between 1 to 2.0 mL/min/kg plant material. This process is continued until the exhaustive extraction of the material and the percolator is kept at room temperature.

Then, the extract is filtered and subjected to evaporation of the solvent on a rotary evaporator at reduced pressure and a maximum temperature of 40° C. This process gives a hydroalcoholic concentrate extract with approximately 29.5% yield.

Example 2. Isolation of the Active Principles of *Bauhinia holophylla*

The fresh leaves from *Bauhinia holophylla* are introduced in to the oven with drying temperature controlled at 45° C. for 72 h. The dried material is pulverized and then triturated in electric knife mill.

Powdered dry leaves (180 g) were extracted with EtOH—$H_2O$ (70:30, v:v) by percolation at room temperature during 72 h. After this the solution was filtrated using cotton. The filtrate was concentrated to dryness under reduced pressure at 40° C. furnishing a hydroalcoholic extract yielding 29.5% of dry weight (53 g).

Figure 1:
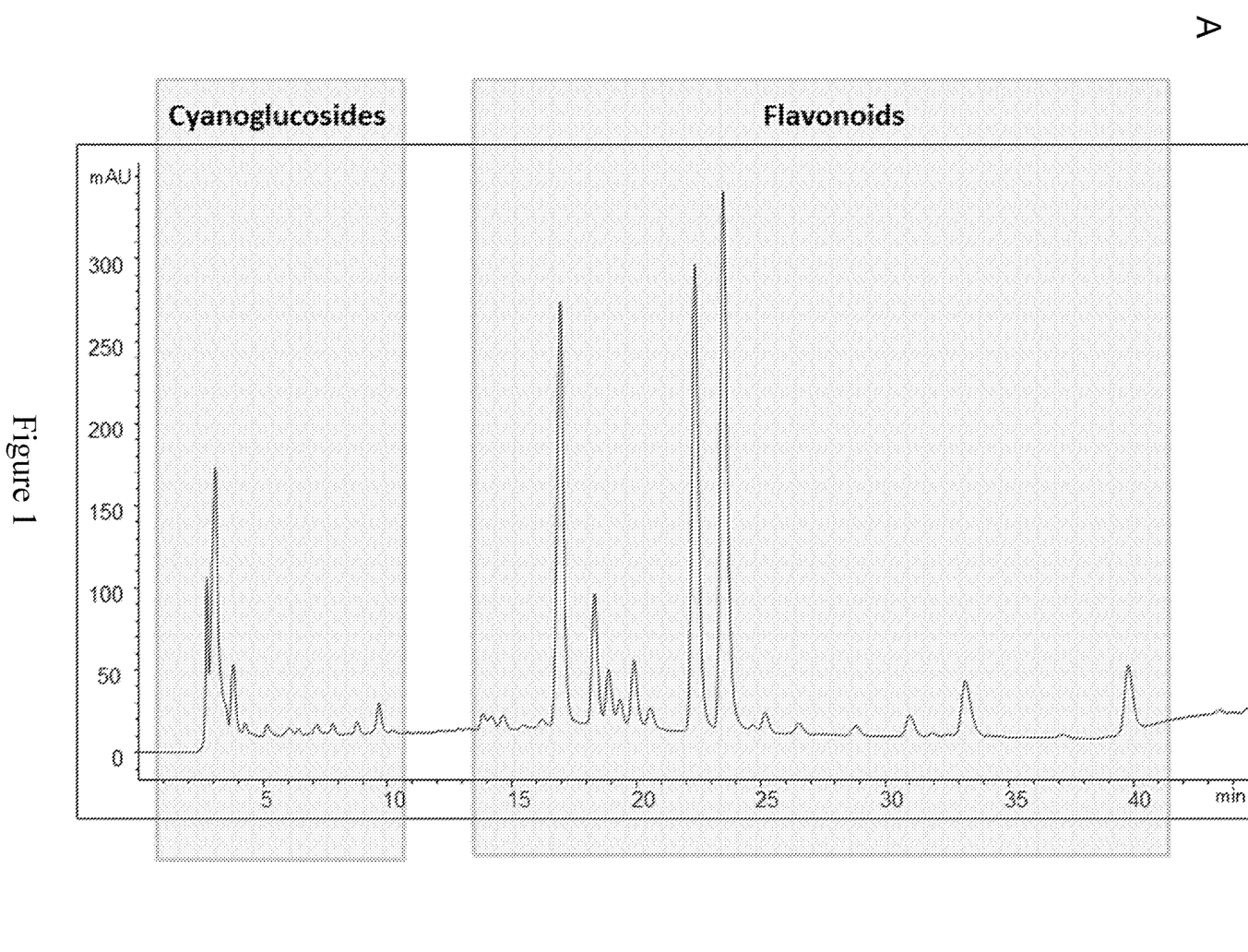
FIG. 1: Characterization of the *Bauhinia holophylla* hydroalcoholic extract as described in Example 1 by liquid chromatography with ultra violet detection (HPLC-UV-DAD) at 254 nm (A) and 366 nm (B) and light scattering detection (HPLC-ELSD)(C) analysis. Grey rectangles represent the cyaoglucosides (left) population and the flavonoids population (right).

The extract was first analysed by high performance liquid chromatography with ultra violet detection (HPLC-UV-DAD) at 254 and 366 nm. Using this technique is possible to highlight the presence of flavonoids with the retention time between 15 and 35 mn (FIG. 1A). The extract was also analysed by HPLC-ELSD (High Performance Liquid Chromatography with Evaporative Light Scattering Detector). Using this detector it is possible to observe the presence of other polar compounds present between the retention time between 0 and 14 mn (FIG. 1B). These compounds are only detected using the ELSD detector, suggesting that they don't have chromophores. Besides that, the ELSD detection clearly suggested that they are present in higher amount compared to the flavonoids in the *Bauhinia holophylla* hydroalcoholic extract.

Based in this observation the isolation of the major compounds was undertaken in order to identify and further to evaluate them in the in vivo hypoglycemic activity. The analytical HPLC conditions were transferred to the MPLC with a gradient transfer method developed in our laboratory for the target isolation of the major compounds (Challal et al, *Planta Medica* 2015, 81(17):1636-1643). The extract was purified by medium pressure liquid chromatography (MPLC) using Zeoprep C18 as the stationary phase (15-25 μm, 460×49 mm i.d., Zeochem) and a linear acidic (0.1% formic acid) MeOH (A) and $H_2O$ (B) gradient (5-33% of A in B over 7:35 h, 33-60% A in B over 9:40 h and 60-100% A in B over 6:40 h, 35° C.). These conditions were optimized on an HPLC column packed with the same stationary phase. The extract, prepared by mixing 15 g of the extract with 45 g of the Zeoprep C18 stationary phase, was introduced into the MPLC column by dry injection. The mixture was conditioned in a dry-load cell (11.5×2.7 cm i.d.). The dry-load cell was connected subsequently between the pumps and the MPLC column. The flow rate was set to 15 mL/min, and UV detection was performed at 254 nm.

Using this approach it was possible to isolate and identify three cyanoglucosides in one step with the following yields: BH-14 (7 mg, 98%), BH-15 (11 mg, 80%) and BH-21 (Lithospermoside, 244 mg, 98%):

BH-14

BH-15

BH-21

The structures of those compounds were elucidated by spectroscopic methods as follows:

BH-14

Amorphous solid; $[\alpha]_D^{21}$ −11, 95° UV $\lambda_{max}$ (log ε) 260 nm; $^1$H-RMN ($D_2O$, 499.9 MHz) and $^{13}$C-NMR ($D_2O$, 125.7 MHz): see Table 1; ESI-MS (negative mode): m/z 328.1 [M−H]$^−$; HRMS: m/z 328.1055 [M−H]$^−$ (calculated $C_{14}H_{18}NO_8$, 328.1032, Δ ppm=7.0). $^1$H and $^{13}$C NMR data (500 MHz, $D_2O$, δ in ppm) are presented in Table 1 below.

TABLE 1

| Position | $^1$H-NMR | $^{13}$C-NMR |
|---|---|---|
| CN |  |  |
| 1 |  | 160.0 |
| 2 | 6.65 (dd, J = 10.1, 2.0) | 126.6 |
| 3 | 6.19 (dt, J = 10.1, 2.0) | 141.3 |
| 4 | 4.42 (dt, J = 8.3, 2.0) | 74.3 |
| 5 | 3.74 (ddd, J = 10.5, 8.3, 2.0) | 79.1 |
| 6 | 4.62 (dd, J = 10.5, 2.0) | 82.1 |
| 7 | 5.85 (t, J = 2.0) | 96.9 |
| 1' | 4.79 (d, J = 7.8) | 106.2 |
| 2' | 3.45 (overlap) | 76.4 |
| 3' | 3.54 (t, J = 9.1) | 78.6 |
| 4' | 3.46 (overlap) | 72.3 |
| 5' | 3.46 (overlap) | 78.8 |
| 6'a | 3.89 (dd, 12.5, 1.6) | 63.3 |
| 6'b | 3.75 (d, J = 12.5) | 63.3 |

BH-15

Amorphous solid; $[\alpha]_D^{21}$ +7.48, 12° UV $\lambda_{max}$ (log ε) 260 nm; $^1$H-NMR ($D_2O$, 499.9 MHz) and $^{13}$C-NMR ($D_2O$, 125.7 MHz): see Table 2; ESI-MS (negative mode): m/z 166.0 [M−H]$^−$; HRMS: m/z 168.0694 [M+H]$^+$ (calculated $C_8H_{10}NO_3$, 168.0661, Δ ppm=14.6). $^1$H and $^{13}$C NMR data (500 MHz, $D_2O$, δ in ppm) are presented in Table 2 below.

TABLE 2

| Position | $^1$H-NMR | $^{13}$C-NMR |
|---|---|---|
| CN |  | 120.7 |
| 1 |  | 162.4 |
| 2 | 6.65 (dd, J = 10.1, 2.0) | 126.6 |
| 3 | 6.18 (dt, J = 10.1, 2.0) | 141.7 |
| 4 | 4.37 (dt, J = 8.1, 2.0) | 74.6 |
| 5 | 3.51 (dd, J = 10.4, 8.1) | 79.7 |
| 6 | 4.31 (dd, J = 10.4, 2.0) | 74.5 |
| 7 | 5.65 (d, J = 2.0) | 95.2 |

BH-21 (Lithospermoside)

Amorphous solid; $[\alpha]_D^{21}$ −209, 12° (c 0.1 MeOH); UV $\lambda_{max}$ (log ε) 260 nm; $^1$H-NMR (D$_2$O, 499.9 MHz) and $^{13}$C-NMR (D$_2$O, 125.7 MHz): see Table 3; ESI-MS (negative mode): m/z 328.1 [M−H]$^-$; HRMS: m/z 328.1059 [M−H]$^-$ (calculated C$_{14}$H$_{18}$NO$_8$, 328.1032, Δ ppm=8.2). $^1$H and $^{13}$C-NMR data (500 MHz, D2O, δ in ppm) are presented in Table 3 below.

TABLE 3

| Position | $^1$H-NMR | $^{13}$C-NMR |
|---|---|---|
| CN |  | 120.5 |
| 1 |  | 158.1 |
| 2 | 6.36 (dd, J = 10.2, 1.8) | 129.8 |
| 3 | 6.14 (dd, J = 10.2, 3.2) | 139.0 |
| 4 | 4.31 (m) | 72.7 |
| 5 | 3.97 (dd, J = 8.2, 6.1) | 76.7 |
| 6 | 4.86 (dd, J = 8.2, 1.7) | 78.6 |
| 7 | 5.65 (t, J = 3.2, 1.7) | 99.9 |
| 1' | 4.90 (dd, J = 7.8) | 102.62 |
| 2' | 3.52 (overlap) | 75.6 |
| 3' | 3.52 (overlap) | 78.7 |
| 4' | 3.44 (overlap) | 72.5 |
| 5' | 3.45 (overlap) | 78.9 |
| 6'a | 3.93 (dd, J = 12.4, 2.1) | 63.7 |
| 6'b | 3.75 (dd, J = 12.4, 5.4) | 63.7 |

Example 3. Evaluation of Pharmacological Activity

The hydroalcoholic extract as obtained in Example 1 and the major compound lithospermoside (BH-21) as obtained in Example 2 were evaluated for their pharmacological activity in reducing fasting blood glucose and improving glucose tolerance in diabetic animals as described below.

The leaves extract obtained under Example 1 was tested at a concentration of 400 mg/kg. The mice were treated daily for days by gavage with the extract as well as metformin (300 mg/kg), and at the end of treatment they underwent an oral glucose tolerance test.

Figure 2:
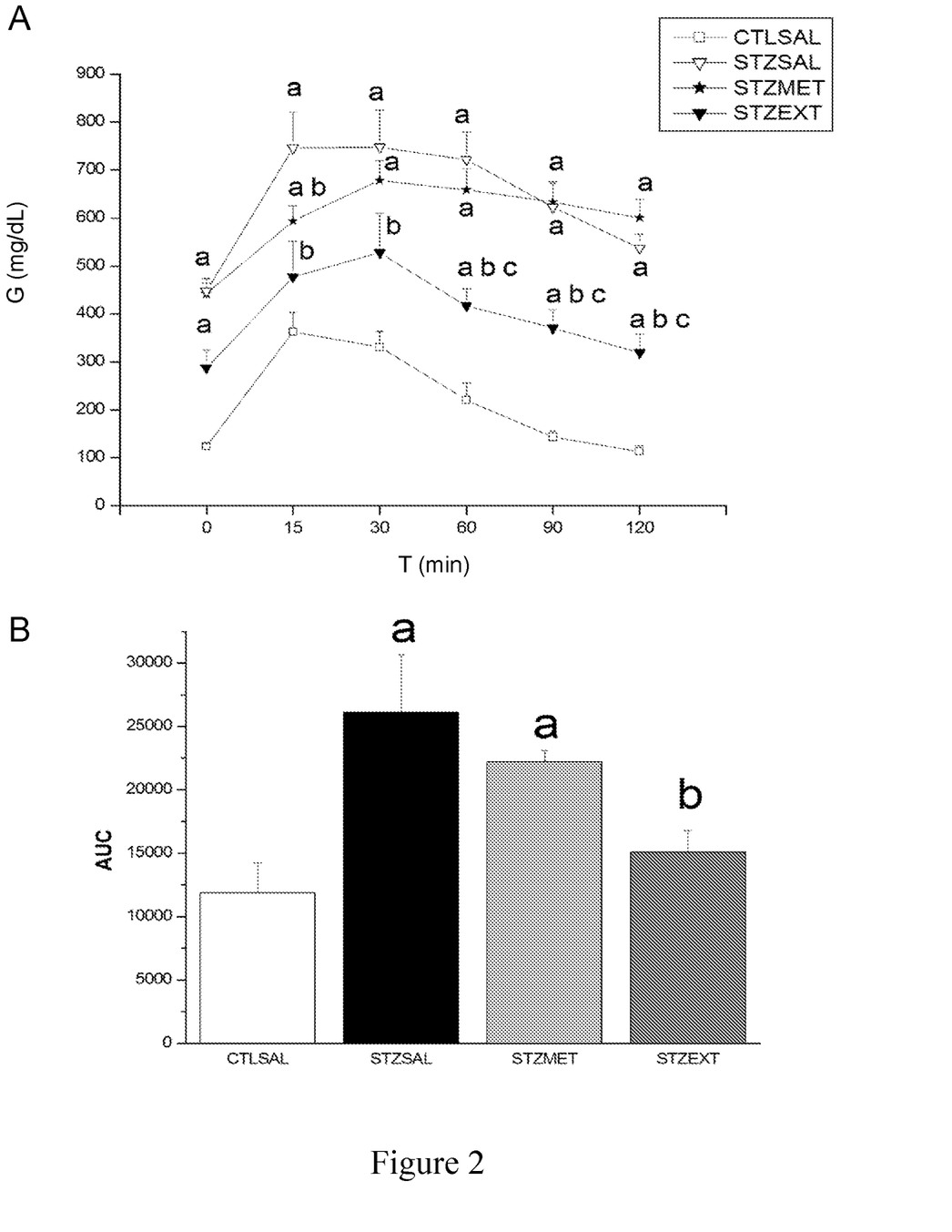
FIG. 2: Effects of 70% EtOH extract on intraperitoneal glucose tolerance test (IpGTT) in mice as described in Example 3; A: Plasma glucose values (G) along the intraperitoneal glucose tolerance test; B: Glucose Tolerance as represented by the area under the curve (AUC) of glycaemia in different groups representing the absorption of glucose. High bars indicate a decrease in glucose absorption which results in glucose intolerance. The animals were treated daily for 14 days. CTLSAL: normoglycemic mice treated orally with saline vehicle, STZSAL: diabetic mice treated orally with saline vehicle, STZMET: diabetic mice treated orally with metformin at the concentration of 300 mg/kg, STZEXT: diabetic mice treated orally with 70% EtOH extract at a concentration of 400 mg/kg. Data expressed as mean±standard error of the mean. ANOVA followed by Tukey posttest. a vs. CTLSAL, b vs. STZSAL, c vs. STZMET, N=8-12, $p<0.05$.

The intraperitoneal glucose tolerance assay (IPGTT) was used to evaluate the glucose disappearance from the plasma of 8-10 hours fasted mice at time 0 and after glucose intraperitoneal injection (2 g/kg) in 15, 30, 60, 90 and 120 min as represented on FIG. 2A where curves represent: CTLSAL: normoglycemic mice treated orally with saline vehicle (0.9% NaCl), STZSAL: diabetic mice treated orally with saline vehicle (0.9% NaCl), STZMET: diabetic mice treated orally with metformin at the concentration of 300 mg/kg, STZEXT: diabetic mice treated orally with 70% EtOH extract at a concentration of 400 mg/kg. FIG. 2B demonstrate mice tolerance for glucose as represented by the absorption of glucose in the same test described above, in normoglycemic mice treated orally with saline vehicle (0.9% NaCl), in treated diabetic mice orally with saline vehicle (0.9% NaCl), in diabetic mice treated orally with metformin at the concentration of 300 mg/kg, in diabetic mice treated orally with EtOH 70% extract at a concentration of 400 mg/kg. Data expressed as mean±standard error of the mean. ANOVA followed by Tukey post test. a vs. CTLSAL, b vs. STZSAL, c vs. STZMET, N=8-12, p<0.05.

The crude extract obtained under Example 1 is able to reduce blood glucose and improve glucose tolerance in diabetic animals with greater efficiency compared to metformin.

Figure 3:
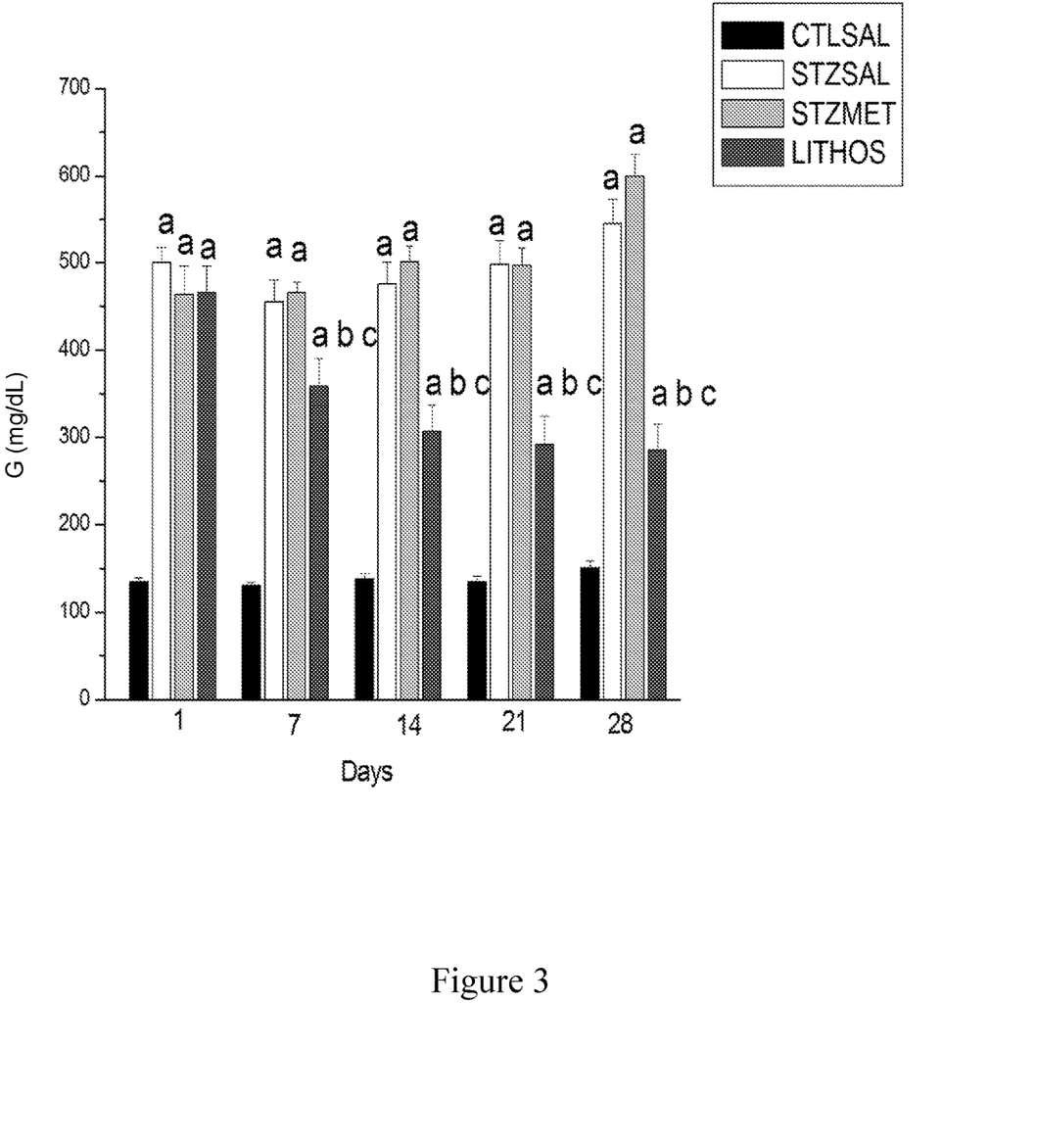
Figure 4:
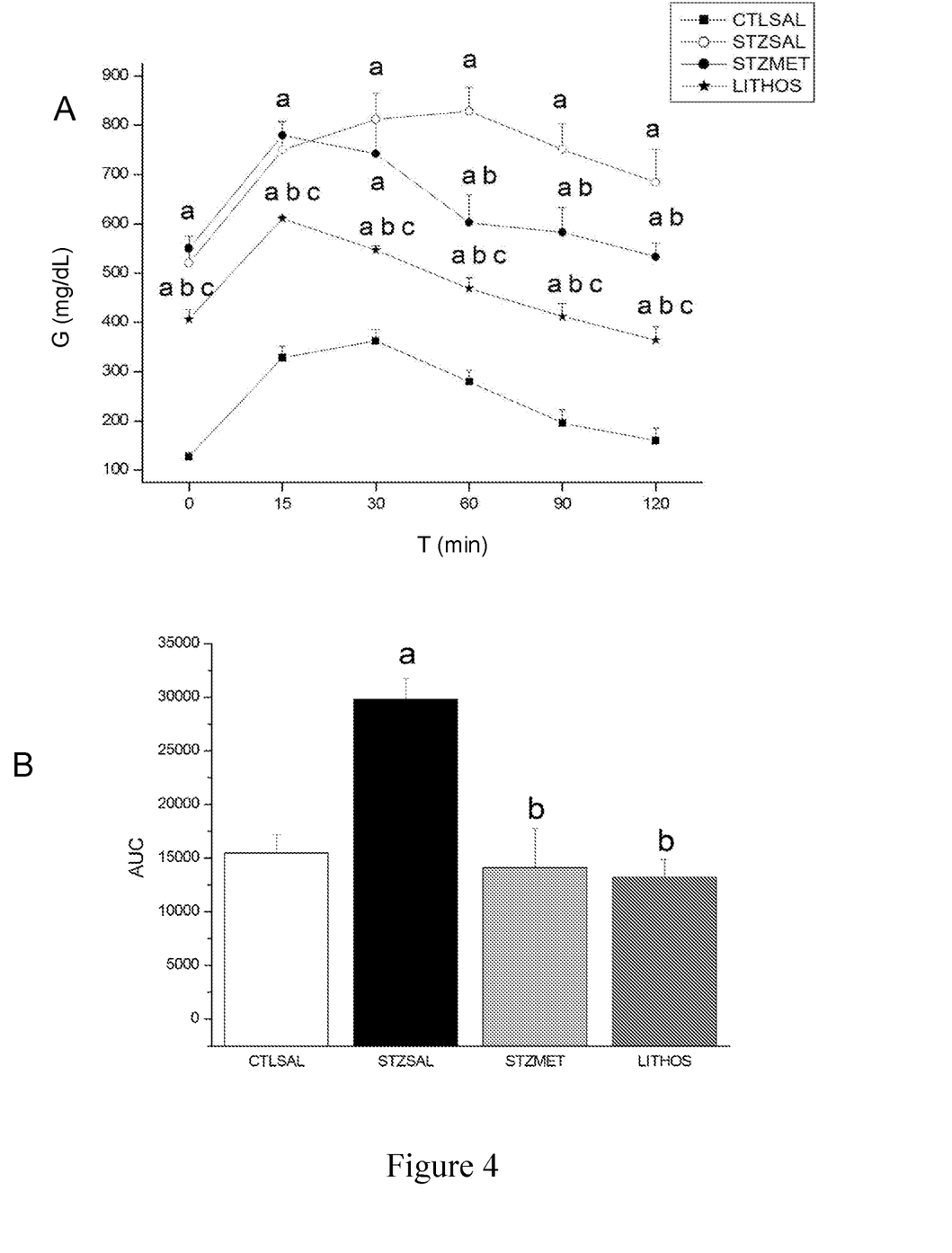
FIG. 4: Plasma glucose concentrations (G) obtained from Intraperitoneal Glucose Tolerance Test (A) and the area under curve (AUC) which indicates the absorption of glucose by the animals (B) as tested in the assay of Example 3. The animals were treated daily for 28 days. CTLSAL: normoglycemic mice treated orally with saline (0.9% NaCl), STZSAL: diabetic mice treated orally with saline (0.9% NaCl), STZMET: diabetic mice treated orally with metformin at the concentration of 300 mg/kg, Lithos: diabetic mice treated with Lithospermoside (BH-21) at a concentration of 10 mg/kg. Data expressed as mean±standard error of the mean. ANOVA followed by Tukey post-test a vs. CTL-SAL, b vs. STZSAL, c vs. STZMET. N=8-12, p<0.05.

The major compound of the cyanoglicoside fraction, BH-21 was tested at a concentration of 10 mg/kg in diabetic mice by gavage daily for 28 days. Male Swiss mice were divided into two groups and treated daily for 28 days by gavage: a control group (CTLSAL) that received saline vehicle (0.9% NaCl) and a group called streptozotocin, previously treated with this drug (150 mg/kg). Animals with blood glucose higher than 250 mg/dl were included in the study and divided into three experimental groups. One group, named streptozotocin saline (STZSAL) received saline (0.9% NaCl); another group of animals treated with metformin (STZMET) at the dose of 300 mg/kg and a third group (LITHOS) received the compound BH-21 (lithospermoside), diluted in saline at a dose of 10 mg/kg body weight. At the end of the treatment period, fasting blood glucose was significantly increased in animals of groups STZSAL and STZMET compared to CTLSAL group (p<0.05). In animals treated with BH-21 (lithospermoside), fasting blood glucose was significantly lower than in STZSAL and STZMET groups but greater than the CTLSAL group (p<0.05) (FIG. 3). In the intraperitoneal glucose tolerance test (IPGTT), the area under the curve (AUC) is significantly higher for the STZSAL group compared to the other three groups (p<0.05). There was no significant difference between STZMET and LITHOS compared to CTLSAL group. However, the LITHOS group blood glucose values were significantly lower than the STZMET group at all times after the intraperitoneal administration of glucose (p<0.05) (FIG. 4A et 4B).

According to the results obtained, it is clear the high potential of the use of lithospermoside thereof for the treatment of patients with diabetes.

The invention claimed is:

1. A method of treating or ameliorating diabetes and/or metabolic syndrome, said method comprising administering in a subject in need thereof a therapeutically effective amount of at least one cyanoglucoside according to Formula (I) tautomers, geometrical isomers, optically active forms, or pharmaceutically acceptable salts thereof or a pharmaceutical formulation thereof:

wherein R$_1$, R$_2$ and R$_3$ are independently selected from an optionally substituted mono- or di-saccharide, —O—R$_4$, —O—C(O)—R$_4$ and halogen, and R$_4$ is selected from H or alkyl.

2. The method according to claim 1, wherein R$^1$ is an optionally substituted monosaccharide.

3. The method according to claim 1, wherein $R_1$ is the following group:

(I')

wherein $R_5$, $R_6$, $R_7$, and $R_8$ are independently selected from H, hydroxyl, amino, —C(O)—$R_9$ and —O—C(O)—$R_9$, and $R_9$ is alkyl.

4. The method according to claim 1, wherein $R^1$ is the following group:

5. The method according to claim 1, wherein $R^1$ is OH.
6. The method according to claim 1, wherein $R^2$ is OH.
7. The method according to claim 1, wherein $R^3$ is OH.
8. The method according to claim 1, wherein the cyanoglucoside is lithospermoside:

(1)

or a tautomer, geometrical isomer, enantiomer, racemic mixture or pharmaceutically acceptable salt thereof.

9. The method according to claim 1, wherein $R_1$, $R_2$ and $R_3$ are OH.

10. The method according to claim 1, said cyanoglucoside having the following structure:

(2)

or tautomers, geometrical isomers, enantiomers and racemic mixtures thereof or pharmaceutically acceptable salts thereof.

11. The method according to claim 1, said cyanoglucoside having the following structure:

(3)

12. The method according to claim 1, wherein diabetes is type 2 diabetes.

13. The method according to claim 1, wherein said cyanoglucoside of Formula (I) or a pharmaceutical formulation thereof is to be administered in combination with at least one co-agent useful in the treatment of diabetes.

14. The method according to claim 1, wherein the patient is suffering from metabolic syndrome.

* * * * *